United States Patent [19]

Josefsson et al.

[11] Patent Number: 4,818,704
[45] Date of Patent: Apr. 4, 1989

[54] METHOD FOR THE SEPARATION AND DETERMINATION OF ENANTIOMERIC AMINE COMPOUNDS USING AN OPTICALLY ACTIVE AGENT

[75] Inventors: Björn Josefsson; Stefan Einarsson, both of Gothenburg; Domingo Sanchez, Floda; Per Möller, Gothenburg, all of Sweden

[73] Assignee: Eka Nobel AB, Surte, Sweden

[21] Appl. No.: 148,139

[22] Filed: Jan. 25, 1988

Related U.S. Application Data

[63] Continuation of Ser. No. 863,712, May 16, 1986, abandoned.

[51] Int. Cl.$^4$ .................... G01N 21/77; G01N 33/68
[52] U.S. Cl. .................................. 436/111; 436/86; 436/89; 436/161; 436/172; 436/175; 436/178; 558/282
[58] Field of Search .................. 436/86, 89, 90, 111, 436/106, 124, 128, 129, 164, 172, 175, 178, 161, 91, 96; 260/349; 548/545; 558/282

[56] References Cited

U.S. PATENT DOCUMENTS

| | | | |
|---|---|---|---|
| 3,835,175 | 9/1974 | Carpino et al. | 558/282 |
| 3,839,396 | 10/1974 | Otsuka et al. | 260/349 X |
| 4,565,877 | 1/1986 | Wada et al. | 436/161 X |

FOREIGN PATENT DOCUMENTS

| | | | |
|---|---|---|---|
| 0010587 | 5/1980 | European Pat. Off. | 260/349 |
| 0048852 | 3/1983 | Japan | 436/161 |
| 0122947 | 7/1984 | Japan | 436/161 |

OTHER PUBLICATIONS

Nimura et al., J. of Chromatography, vol. 352, pp. 169–177, 1986.
Einarsson et al., J. of Chromatography, vol. 282, pp. 609–618, 1983.
Aswad, Anal. Biochem., vol. 137, No. 2, pp. 405–409, 1984.
Davankov, Soviet Science Review, vol. 3, No. 6, pp. 352–356, 1972.
Moye et al., Analytical Letters, vol. 12, pp. 25–35, 1979.
Carpino et al., J. Org. Chem., vol. 37, No. 22, pp. 3404–3409, 1972.
Glass, J. Agric. Food Chem., vol. 31, pp. 280–282, 1983.
Roseboom et al., Anal. Chim. Acta, vol. 135, No. 2, pp. 373–377, 1982.

*Primary Examiner*—Barry S. Richman
*Assistant Examiner*—Robert J. Hill, Jr.
*Attorney, Agent, or Firm*—Holman & Stern

[57] ABSTRACT

The invention relates to a new chiral reagent of the formula

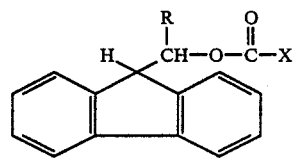

wherein X is halogen, an azide group or a succinimidyl group and wherein R is an alkyl group or a trifluormethyl group. The invention further relates to a method for the derivatization, determination and preparation resolution of primary and secondary amino-containing compounds. The method comprises the steps of derivatizing the amino function by the reagent to form diastereomeric carbamates, which are determined by e.g. fluorimetry or absorptiometry after separation by liquid chromatography.

6 Claims, 4 Drawing Sheets

METHOD FOR THE SEPARATION AND DETERMINATION OF ENANTIOMERIC AMINE COMPOUNDS USING AN OPTICALLY ACTIVE AGENT

This is a continuation of U.S. patent application Ser. No. 863,712, filed May 16, 1986, now abandoned.

BACKGROUND OF THE INVENTION

1. Field of the Invention

This invention relates to an improvement in enantiomeric separation and detection by means of a chiral reagent and high performance liquid chromatography (HPLC). More specifically, it relates to an optically active fluorenyl chloroformate which forms stable diastereomeric carbamates with primary and secondary amines in a quantitative way. This product can be detected by fluorimetry or by absorptiometry after separation on an HPLC column.

2. Description of the Background Art

The separation of optically active amino-containing substances is of great importance in biological research and pharmaceutical chemistry. These substances are common in pharmaceuticals and many of these substances are enantiomers occurring as racemic mixtures. In many cases the biological activity of these enantiomers is attributed to the conformation of one particular optically active antipode. Therefore, it is very important to distinguish or resolve the enantiomers of such substances.

For quantitive purposes, it is desirable to use chromatographic methods to separate these substances. These methods offer many advantages including the utilization of small sample sizes, simple pretreatment procedures, and high sensitivity of detection.

Since the first chromatographic separation of optically active isomers was performed in 1951 with a paper chromatography technique, a great number of such methods have been introduced. Some of these methods have recently been reviewed in books including: Souter, R. W. "Chromatographic Separation of Stereoisomers"; CRC Press, Boca Raton, 1985; and Jacques, J. et al., "Enantiomers, Racemates and Resolutions"; John Wiley & Sons; New York, 1981.

The resolution of enantiomers requires the intervention of a chiral agent. Chromatographic resolving methods have been developed in two major directions:

1. Direct resolution of enantiomers in columns with either a chiral stationary phase (CSP) or a chiral component in the mobile phase; and
2. Indirect resolution of formed diastereomers after derivatization with a chiral reagent.

The liquid chromatographic direct separation of enantiomers on chiral stationary phases has received a great deal of attention. Currently, there are some commercially available chiral columns. Recent efforts have focused on the feasability of making a chiral stationary phase for separating as many different types of chiral substances as possible. Still very few amine and amino acids are available that have been directly resolved on chiral columns of any type, without previous derivatization.

Tamegai et al., J. Liq. Chromatography, 1979, 2, 1229 have reviewed methods based on indirect resolution of enantiomers by derivatization with a chiral reagent to form diastereomers which are resolved on conventional columns. Furukawa et al., Chem. Phar. Bul 1975, 23, 1623 were the first to separate enantiomeric amino acids using readily available (+)-10-camphor sulphonyl chloride as a chiral reagent. The carbonyl residue was then transformed in a second step into the p-nitrobenzylester which resulted in derivatives sensitive to UV-detection.

The most common chiral reagents for selective amine function derivatization are those based on isothiocyanate which give UV sensitive thiourea derivatives with primary and secondary amines. The reaction is effected under weakly basic conditions for about 20 minutes at room temperature without formation of by-products.

The most successful reagent of this kind is 2,3,4,6-tert-o-acetyl-p-d-gluco-pyranosyl isothiocyanate (GITC), which is used for both amino acids and amines. The resulting thiourea derivatives of most protein amino acids can be resolved with this reagent on a conventional, reversed phase column within two hours. The resolution obtained is preferably due to the lipophilic nature of the sugar residue combined with conformational rigidity.

Fluorescence chiral derivatization regents for amino containing compounds are rare and only reagents based on 0-phthalaldehyde combined with chiral thiols (OPA) are reported, JP 60 38, 652 (85 38, 652). The different chiral thiol compounds which have been used are N-acetyl-L-cysteine and acetyl-L-cysteine. These compounds yield diastereomeric isoindols with primary amino groups. The reaction is selective and completed within a minute at room temperature in a buffered water mixture without racemization. The formed diastereomers are, however, not stable.

These are some essential and desirable conditions such a reagent should have.

1. It has to be optically pure.
2. It has to contain a chromophore or a fluorophor.
3. The reaction conditions should be mild, otherwise the risk of potential racemization will increase.
4. The reagent should react with primary and secondary amino groups.
5. The resulting diastereomers should be stable.
6. The resulting diastereomers should separate on conventional HPLC columns.
7. The method should be applicable on a preparative scale.
8. The method should be feasible to automate.

There has not been a disclosure or suggestion of a chiral reagent combined with a method which effectively derivatize, detect, and separate racemic mixtures of primary and secondary amino-containing compounds.

SUMMARY OF THE INVENTION

The object of the present invention is to provide a chiral reagent and a method for indirect resolution of primary and secondary amino-containing compounds on conventional reversed phase HPLC columns. The reagent should give fluorescent derivatives which are stable and detectable by fluorometry or absorptiometry after separation by liquid chromatography. A stable derivative facilitates quantitation and automation. Furthermore, the reaction should occur rapidly under mild conditions in aqueous phase and without racemization.

The object of the invention has been achieved by derivatizing the amino function of the compounds by adding an optically active reagent of the formula:

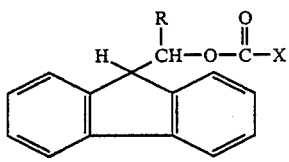

wherein X is a halogen, an azide group, or a succinimidyl group and wherein R is an alkyl group or a trifluoromethyl group, to form diastereomoeric carbamates which are determined by per se known methods, e.g., fluorimetry or absorptiometry, after separation by liquid chromatography.

The reagent performs:

1. The determination of optical purity in resolved amines and amino acids;
2. The determination of different amounts of enantiomeric amino-containing compounds in biological systems; and
3. Preparative resolution of amino-containing racemic mixtures.

DETAILED DESCRIPTION OF THE INVENTION

The invention is based on the rapid reaction of chloroformates with different amines to form stable carbamates during Schotten-Bauman conditions. The reaction is performed in one step within seconds at room temperature. In a certain pH range, the reaction is selective to amino functions and the only formed by-product is the corresponding alcohol. The reagent excess is easy to handle so that the interference in the following separation step is omitted.

The 9-fluorenylmethylchloroformate reagent (FMOC) is fluorescent with excitating emission wavelengths of 270/315 mm. The formed products are selectively detected at these wavelengths. This property together with the selective reaction of the reagents provide very complex mixtures wherein body fluids can be handled without any clean-up or pretreatment procedure.

The invention synthesizes an optically active reagent which can be used in the same way as the achiral FMOC-reagent with its many advantages so as to form diastereomers with racemic amino-containing compounds. The diastereomers can be resolved with a conventional separation system that is typically reversed phase HPLC. Reversed phase HPLC is the most common and effective LC separation system for trace analysis and preparative separation. Making the reagent optically active is certainly not a guarantee for obtaining resolvable diastereomers. The introduction of an asymmetric carbon atom must be carried out at a position so that the reagent properties are maintained.

The invention creates chirality of the FMOC reagent by introducing an asymmetric carbon atom at the 9-fluorenyl-1 position. This type of compound has not been described before in the literature. This position is strategic while it is close to the formed amid function as well as to the rigid cyclic arrangement representing the fluorene moiety. It should be pointed out that there are still no general rules to design chiral reagents which are amenable for successful resolution of diastereomers. Therefore, it is not possible to make predictions. Thus, optical resolution is still based on trial and error experiments. However, surprisingly the 9-fluorenyl-1-ethylchloroformate reagent (FLEC) yields diastereomers with most amines resolvable on reversed phase LC columns. Furthermore, the (+)-1-(9-fluorenyl) ethylchloroformate gave diastereomers of the rare D-amino acids which were separated from the predominant L-form. The properties of the new reagent were maintained compared to the achiral FMOC reagent. As a conclusion, a new reagent is described which will be very practical and useful for the determination of optically active amino containing compounds in complete mixtures and for the preparative resolution of amines.

Figure 1:
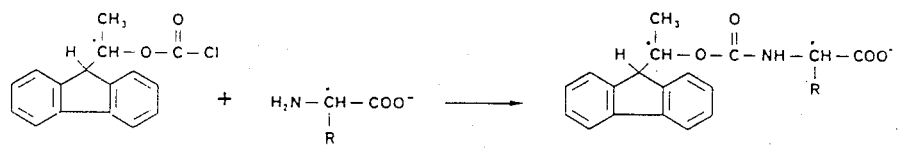
FIG. 1 shows a reagent and reaction scheme.

The reaction of FLEC with amino acids proceeds as shown in FIG. 1. The reagent also reacts with water to yield the corresponding alcohol as a hydrolysis product.

Synthesis of (+)-1-(9-fluorenyl)ethyl chloroformate (FLEC)

Synthesis of 1-(9-fluorenyl)ethanol: To a solution of 8.3 g fluorene in 100 ml of dry ether 31 ml BuLi (1.6M in hexane) was added. The mixture was refluxed for 30 minutes and then cooled in an ice bath. To the resulting mixture a solution of 2.8 ml acetaldehyde in 40 ml dry ether was added during 15 minutes and the refluxed for 1 hour. Water (100 ml) was added and the ether layer collected in a separatory funnel, dried with MgSO$_4$, and evaporated. The product was further purified by flash-chromatography and recrystallized from ligrion (b.p. 80°–110° C.) to give white needles, m.p. 101°–103° C., mass spectrum M+ m/e 210.15, $^1$H NMR(CDCl$_3$), 0.87 (d, 3H), 1.70 (s, 1H), 4.09 (d, 1H), 4.35–4.65 (m, 1H), 7.15–7.85 (m, 8H).

Optical resolution of 1-(9-fluorenyl)ethanol: To a solution of 4.0 g 1-(9-fluorenyl)ethanol in 25 ml anhydrous pyridine, and equimolar amount of (−)-camphanic acid chloride (4.12 g) was added, and the mixture was stirred at room temperature for 3 hours. The solution was poured into ice-water and extracted with CH$_2$Cl$_2$. The CH$_2$Cl$_2$-layer was washed with dilute hydrochloric acid, dried (mGSO$_4$) and evaporated to dryness. The crude ester was dissolved in 200 ml MeOH and cooled to −15° C. Deposited crystals (fraction A) were crystallized twice from the same solvent giving 1.0 g of the less soluble diastereomeric ester in pure form, (m.p. 159°–160° C., (racemate m.p. 152° C.). The optical purity of the diastereomeric ester was checked on a chiral stationary phase ((−)-dinitrobenzoyl-phenylglycine coupled to aminopropylsilica, Pirkle's phase) and it was greater than 99 percent.

Hydrolysis of the ester: To a solution of the optically pure diastereomeric ester (1.0 g) in 50 ml dry ether, 0.8

LiAlH₄ was added. The mixture was stirred at room temperature for 1 hour giving the alcohol after work up, m.p. 91° to 93° C. (decomp.).

(+)-1-(9-fluorenyl)ethyl chloroformate: To a solution of phosgene (0.8, 8.1 mmol) in 15 ml of dry toluene cooled to 0° C., a solution of optically pure alcohol (0.44 g, 2.1 mmol) and triethylamine (0.30 ml, 2.1 mmol) in 20 ml dry toluene, was added dropwise. After addition was completed, stirring was continued for 2 hours at 0° C. The triethylaminehydrochloride was them removed by filtration and the filtrate was concentrated at reduced pressure giving an oil.

$[\alpha]_D^{25} = +67.9°$ (CH₂Cl₂, C=1)
$[\alpha]_{578}^{25} = +70.5°$ (CH₂Cl₂, C=1)
¹H NMR (CDCl₃): 0.76 (d, 3H), 4.30 (d, 1H), 5.47–5.75 (m, 1H), 7.18–7.75 (m, 8H)

Anal. calcd for C₁₆H₁₃O₂Cl: C, 70.46; H, 4.80; Cl, 13.00 Found: C, 70.64; H, 4.80; Cl, 13.13

EXPERIMENTAL CONDITIONS

Solvents and reagents: Acetonitrile, tetrahydrofurane and acetone were purchased from Rathburn (Walkerburn, U. K.). The amino acid standards and the FMOC-Cl reagent were obtained from Sigma (St. Louis, MO, U.S.A.). The elution buffer was made of acetic acid in double distilled water (3 mL/L), titrated to the appropriate pH with sodium hydroxide. The FLEC-Cl reagent was dissolved in acetonityrile:acetone (1:3) and had a concentration of 15 mmol/L. The reaction buffer was made of boric acid (1M) and the pH was adjusted with sodium hydroxide.

Derivatization: Sample (0.4 mL) and buffer (0.1 mL, pH) are mixed in a 3 ml reaction vial. The reagent (0.5 mL) is added and allowed to react. After 1 minute the vial is almost filled with pentane and the reaction mixture is extracted to remove excess reagent. The extraction is repeated twice, and then the aqueous phase is ready for injection.

Figure 2:
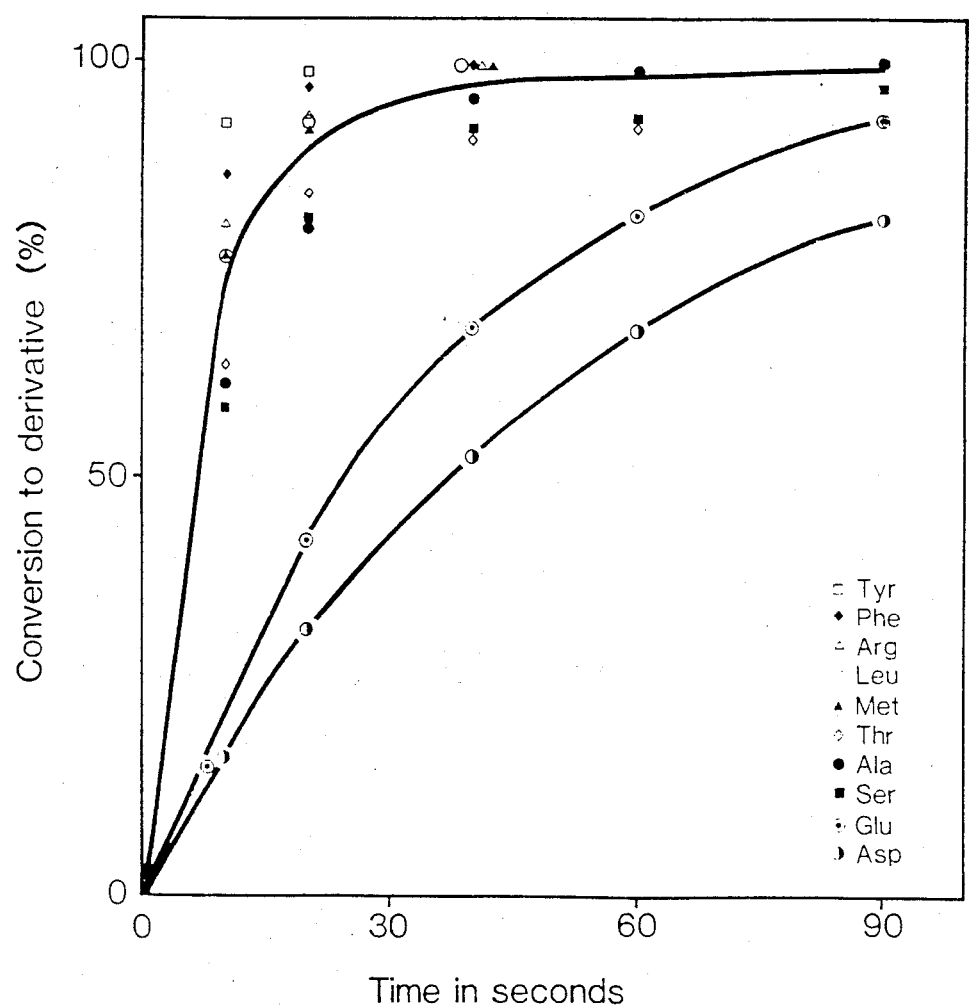
FIG. 2 is a graph showing reaction rates and yields to form fluorescent diastereomeric carbarmates of different amino acids.

Reaction rate: The rate of the reaction of the amino acids with the FLEC-Cl reagent is shown in FIG. 2 and was determined by derivatization of the amino acids (one at a time) in the usual manner with the reagent at pH 8.03 (sample plus buffer). After a certain time interval the reaction was stopped by addition of acetic acid, and the excess of the FLEC-Cl reagent was removed by pentane extractions. The amount that remained unreacted was determined by precolumn derivatization with 0-phtalaldenyde/mercaptoethanol, followed by liquid chromatography. The results were compared with a solution treated in the same way, but without the FLEC-Cl reagent (original amount of amino acid), from which the conversion to a FLEC-derivative could be calculated. Each point is a mean of two measurements.

Figure 3:
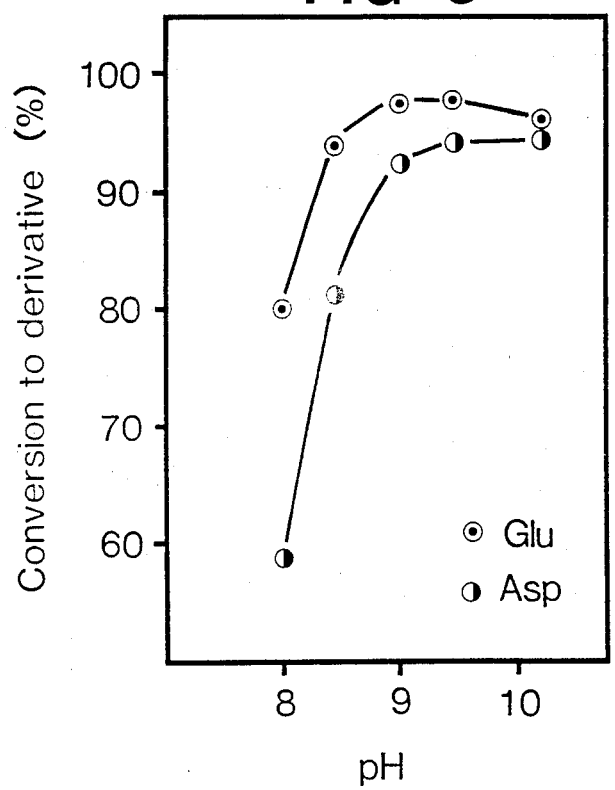
FIG. 3 is a graph showing reaction yields vs. pH for asparagine acid and glutamine acid.

The effect of pH on the reaction rates of aspartic acid and glutamic acid is shown in FIG. 3 and was carried out in the same way as described above with a 1 minute reaction time. Measurements were made at pH 8.01, 8.46, 9.01, 9.47 and 10.23. The pH was measured in the reaction solution after the addition of the buffer.

The reactive reaction rates of the FLEC-Cl and the FMOC-Cl reagents with valine, glutamic acid, proline, and lysine were determined by comparison of the yield obtained when a standard amino acid solution was derivatized with each of the reagents. The results were obtained with a mixed FLEC/FMOC reagent. The derivatives were repeated with chromatography and the peak areas were compared.

Figure 4:
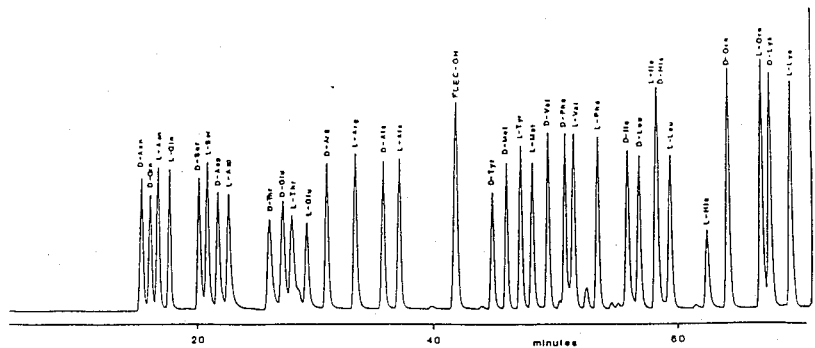
FIG. 4 is a chromatogram showing the resolution of 17 amino acids as fluorescent labeled diastereomeric carbamates performed with reversed phase liquid chromatography.

FIG. 4 shows the resolution of 17 amino acids as fluorescent labelled diastereomeric carbamates. The resolution is performed with reversed phase liquid chromatography.

Experimental conditions were:

The FLEC-Cl reagent is dissolved in acetonitrile-/acetone (1/4), 15 mM. The reaction buffer is a borate buffer, 1M, pH 6.5.

0.4 ml sample and 0.1 ml borate buffer are mixed. To this solution is added 0.5 ml of the reagent. After 1 minute reaction time the mixture is extracted 3 times with pentane. The pentane extracts are discarded and the aqueous phase is ready for injection. When derivatizing relatively hydrophobic amines not having an acid group, the extraction step is omitted and the excess reagent is removed by reaction with a hydrophilic amine, typically hydroxyproline or hydrazine.

TABLE 1

| Time (min) | Gradient elution: | | |
|---|---|---|---|
| | % AcN | % THF | % Buffer |
| 0 | 8 | 17 | 75 |
| 8 | 8 | 17 | 75 |
| 22 | 0 | 30 | 70 |
| 70 | 0 | 50 | 50 |

Separation conditions (amino acids):
Column: 150 × 4.6 mm packed with octyl material sold under the trade name Spherisorb.
d = 3 um. Elution buffer: Acetic acid 3 promille, pH 4.35. Flow rate: 0.3 ml/min.

In table II below are stated the k'-values and resolution factors, α-values for some amino-containing pharmaceuticals.

TABLE II

| Amine | k'₁ | k'₂ | α |
|---|---|---|---|
| Metoprolol | 6.8 | 7.5 | 1.1 (1) |
| Tokainid | 9.4 | 10 | 1.06 (2) |
| Norephedrine | 5.03 | 5.28 | 1.05 (3) |

Figure 5:
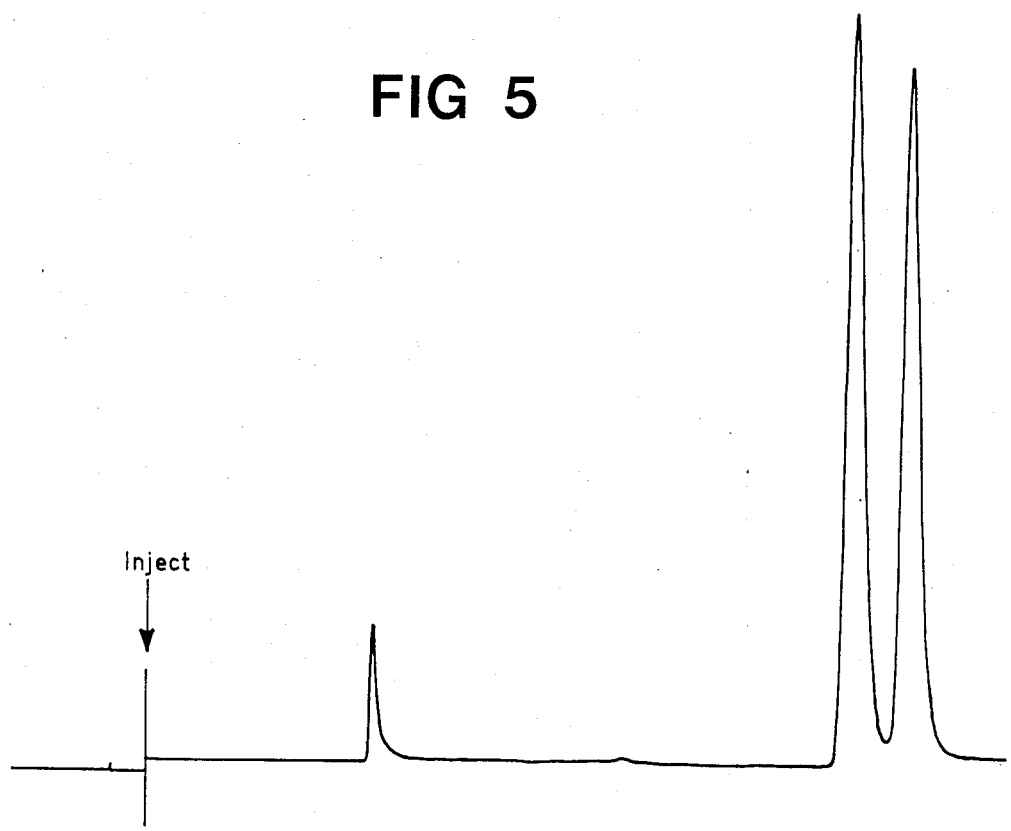
FIG. 5 is a chromatogram showing the resolution of racemic metoprolol.

Column: 250 × 4.6 mm, packed with Spherisorb octyl material.
d = 5 um, Flow rate: 1.2 ml/min.
Elution conditions:
(1) 60% Acetonitrile, 40% water
(2) 50% Acetonitrile, 50% water
(3) 55% THF (tetrahydrofurane), 45% water FIG. 5 shows the resolution of a racemic solution of metoprolol, a cardioselective B-adrenoceptor antagonist (B-blocker), derivatized with a racemic FLEC-Cl reagent. Colume: 4.6×250 mm, packed with 5 um octyl material (Spherisorb): Eluent: 60% acetonitrile, 40% water.

Figure 6:
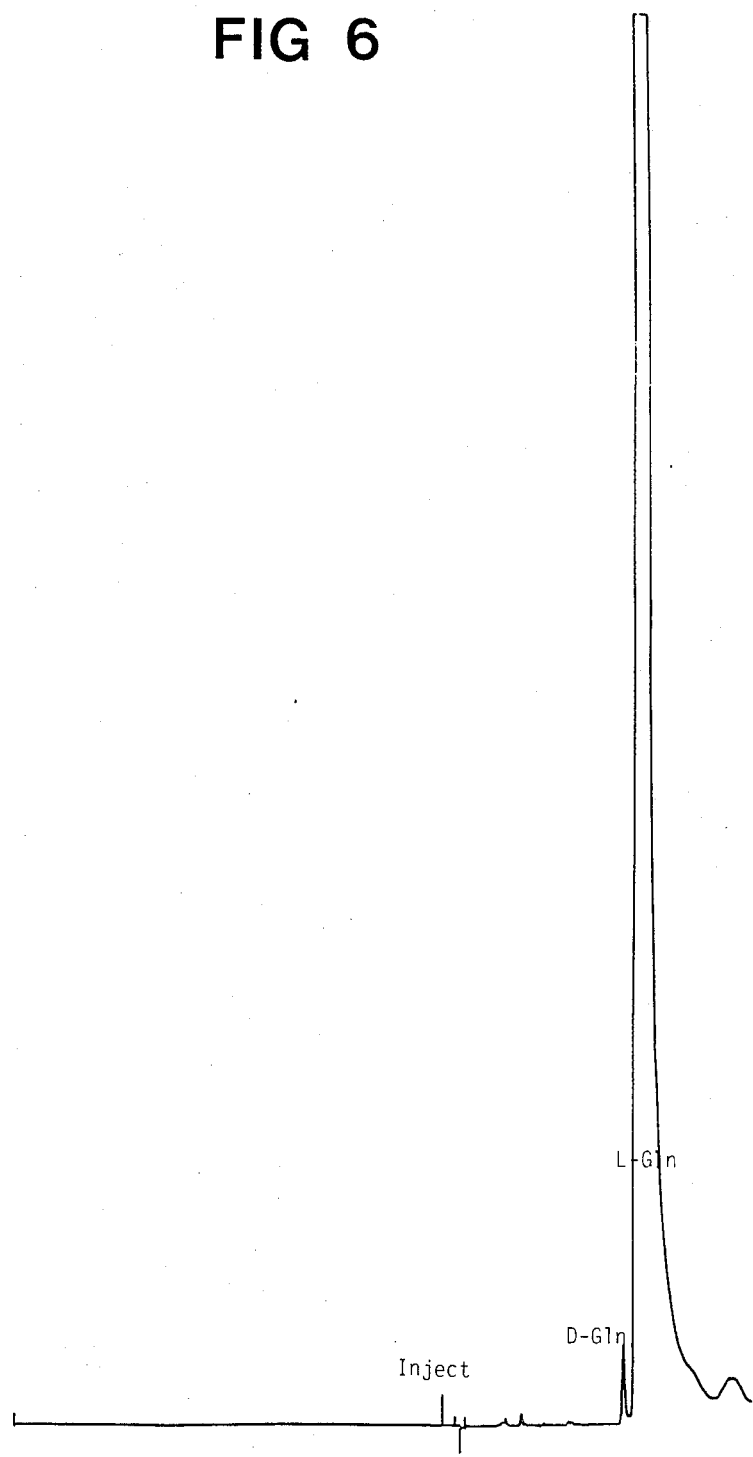
FIG. 6 is a chromotogram showing derivatization and resolution of commercially available "optically pure" L-glutamine.

FIG. 6 shows the derivatization and resolution of commercially available "optically pure" L-glutamine to determine the combined effect of optical purity of the amino acid standard, the optical purity of the reagent, and the racemization of the derivatization. L-glutamine (1 mmol/1) was derivatized with FLEC-Cl. The D-glutamine peak amounts to 0.6 promille of the L-glutamine and was determined by standard addition of a small amount of D-glutamine (2 umol/1).

In Table III below are stated the k' and resolution factors, α-values, for the common peptide amino acids separated on reversed phase column.

TABLE III

| Amino acid | k'₁ | k'₂ | α | |
|---|---|---|---|---|
| Aspargine | 1.34 | 1.46 | 1.09 | I |
| Glutamine | 1.29 | 1.46 | 1.13 | |
| Serine | 2.01 | 2.09 | 1.04 | |
| Aspartic acid | 2.37 | 2.54 | 1.07 | |
| Threonine | 2.94 | 3.31 | 1.13 | |

TABLE III-continued

| Amino acid | $k'_1$ | $k'_2$ | $\alpha$ | |
|---|---|---|---|---|
| Glutamic acid | 3.26 | 3.69 | 1.13 | |
| Arginine | 3.54 | 4.03 | 1.14 | |
| Alanine | 5.63 | 6.20 | 1.10 | |
| Proline | 5.51 | 5.51 | 1.00 | |
| Tyrosine | 3.29 | 3.91 | 1.19 | II |
| Methionine | 3.57 | 4.29 | 1.20 | |
| Phenylalanine | 4.83 | 6.09 | 1.26 | |
| Valine | 5.00 | 5.91 | 1.18 | |
| Isoleucine | 8.17 | 9.69 | 1.19 | |
| Leucine | 8.46 | 10.20 | 1.21 | |
| Histidine | 3.37 | 4.77 | 1.42 | III |
| Ornithine | 5.37 | 6.69 | 1.25 | |
| Lysine | 7.23 | 8.37 | 1.16 | |

Eluent composition:
I 35% THF, 65% Acetic acid buffer (3%, pH 4.35)
II 40% THF, 60% Acetic acid buffer (3%, pH 4.35)
III 45% THF, 55% Acetic acid buffer (3%, pH 4.35)
Column: 4.6 × 250 mm, packed with 5 um octyl material (sold under the trade name of Spherisorb)

As indicated above reagent excess can be removed by different methods. One method, preferably used when separating amines, is to react reagent excess with an amine yielding a product which does not interfere during the separation with the compounds to be determined. The amine as well as the derivative should be water-soluble. Examples of such amines are hydroxyproline and hydrazine.

Another method preferably used when separating amino acids or amino sugars that form hydrophilic amino derivatives, is to extract reagent excess with a solvent of low polarity, e.g. pentane or hexane.

The reagent according to the present invention is also applicable for preparative resolution of amino-containing racemic mixtures. After separation of the derivatives by HPLC, the amino-containing compounds are regained by conventional methods, such as acid or basic hydrolysis or by hydrogenolysis.

In Table IV below a comparison of current precolumn derivatizing agents and FLEC-Cl is made which illustrates the superiority of the FLEC-reagent.

TABLE IV

| | FLEC | PITC GITC | OPA | Dansyl Dabsyl |
|---|---|---|---|---|
| Primary and secondary amino compounds | Yes | Yes | No | Yes |
| Automated | Possible | No | Yes | No |
| Stable derivatives | Yes | No | No | No |
| MDQ | 100-200 femtomoles | 1-10 picomoles | 100-200 femtomoles | 100-200 femtomoles |
| Major interferences | No | No | No | |

Although 1-(9-fluorenyl)ethyl chloroformate is the only reagent described by way of examples there are a number of structural analogues that may be used as well. Methyl as R in the general formula in claim 1 could be substituted by trifluormethyl or a higher alkyl group. Instead of chlorine, X could be bromine, an azide group or a succinimidyl group, which have been tested with the FMOC-reagent and found to be good leaving groups.

We claim:

1. A method for the resolution and determination of compounds having an amino function in aqueous and non-aqueous samples, comprising adding an optically active agent of the formula:

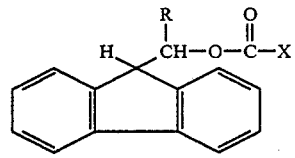

wherein X is halogen, and azide group or a sucinimidyl group and wherein R is an alkyl group or a trifluoromethyl group to a sample containing compounds having an amino function so as to derivatize the amino function of the compounds and form diastereomeric carbamate derivatives, and then separating and determining said derivatives by liquid chromatography.

2. The method as claimed in claim 1 further comprising reacting excess agent with an amine to yield a product which does not interfere with the separation and determination of the carbamate derivatives.

3. The method as claimed in claim 1, wherein excess agent is extracted away with a solvent of low polarity.

4. The method as claimed in claim 1, wherein R is a methyl group.

5. The method as claimed in claim 4, wherein X is chloride.

6. A method for the resolution and determination of compounds having an amino function in aqueous and non-aqueous samples, comprising adding optically active 1-(9-fluorenyl)ethyl chloroformate to a sample containing compounds having an amino function to derivatize the amino function of the compounds and form diastereomeric carbamate derivatives of the 1-(9-fluorenyl)ethyl chloroformate and then separating and determining said derivatives by liquid chromatography.

* * * * *